(12) United States Patent
Brahm (10) Patent No.: US 10,905,800 B1
(45) Date of Patent: Feb. 2, 2021

(54) OCULAR COVERING AND METHOD OF USE

(71) Applicant: BioDlogics, LLC, Cordova, TN (US)

(72) Inventor: Timothy R. Brahm, Germantown, TN (US)

(73) Assignee: BioDlogics, LLC, Cordova, TN (US)

( * ) Notice: Subject to any disclaimer, the term of this patent is extended or adjusted under 35 U.S.C. 154(b) by 0 days.

(21) Appl. No.: 14/167,332

(22) Filed: Jan. 29, 2014

Related U.S. Application Data (60) Provisional application No. 61/757,862, filed on Jan. 29, 2013.

(51) Int. Cl.
| | | |
|---|---|---|
| *A61L 27/36* | (2006.01) | |
| *A61F 9/00* | (2006.01) | |
| *A61L 27/54* | (2006.01) | |

(52) U.S. Cl.
CPC ........ *A61L 27/3641* (2013.01); *A61F 9/0017* (2013.01); *A61L 27/3604* (2013.01); *A61L 27/54* (2013.01)

(58) Field of Classification Search
CPC .................................................. A61F 9/0017
See application file for complete search history.

(56) References Cited

U.S. PATENT DOCUMENTS

| | | | |
|---|---|---|---|
| 4,120,649 A | 10/1978 | Schechter | |
| 4,361,552 A | 11/1982 | Baur, Jr. | |
| 4,674,488 A | 6/1987 | Campbell | |
| 4,894,063 A | 1/1990 | Nashef | |
| 5,607,590 A | 3/1997 | Shimizu | |
| 5,618,312 A | 4/1997 | Yui | |
| 6,152,142 A | 11/2000 | Tseng | |
| 6,254,637 B1 | 7/2001 | Lee | |
| 6,326,019 B1 | 12/2001 | Tseng | |
| 7,494,802 B2 | 2/2009 | Tseng et al. | |
| 7,824,671 B2 | 11/2010 | Binder et al. | |
| 8,071,135 B2 | 12/2011 | Liu et al. | |
| 2001/0053839 A1 | 12/2001 | Noishiki | |
| 2003/0187515 A1 | 10/2003 | Hariri | |
| 2003/0225355 A1 | 12/2003 | Butler | |
| 2004/0048796 A1 | 3/2004 | Hariri | |
| 2007/0021762 A1 | 1/2007 | Liu et al. | |
| 2007/0031471 A1 | 2/2007 | Peyman | |
| 2007/0038298 A1 | 2/2007 | Sulner | |
| 2008/0044848 A1 | 2/2008 | Heidaran | |
| 2008/0046095 A1 | 2/2008 | Daniel | |
| 2008/0131522 A1 | 6/2008 | Liu et al. | |
| 2008/0193554 A1 | 8/2008 | Dua | |
| 2008/0274184 A1 | 11/2008 | Hunt | |
| 2009/0208551 A1 | 8/2009 | Jung | |
| 2010/0104539 A1 | 4/2010 | Spencer | |
| 2010/0106233 A1 | 4/2010 | Deeken | |
| 2011/0129520 A1 | 6/2011 | Blood | |
| 2011/0189301 A1* | 8/2011 | Yang | B29C 63/02 424/582 |
| 2012/0009644 A1 | 1/2012 | Goldstein | |
| 2012/0009679 A1 | 1/2012 | Walsh | |
| 2012/0078378 A1 | 3/2012 | Spencer | |
| 2012/0083900 A1 | 4/2012 | Wilkins | |

FOREIGN PATENT DOCUMENTS

| | | |
|---|---|---|
| EP | 0781564 A2 | 7/1997 |
| WO | 2009044408 A1 | 4/2009 |
| WO | 2012003377 A2 | 1/2012 |
| WO | 2012112417 A2 | 8/2012 |
| WO | 2012112441 A1 | 8/2012 |

OTHER PUBLICATIONS

Tseng et al. "Amniotic Membrane in Ophthalmology" from opthalmology.web, Posting Date: Dec. 23, 2008. Retrieved from the Internet on: Aug. 31, 2018]. Retrieved from: <URL: https://web.archive.org/web/20080821120552/http://www.oktoophtho.com/eyecare/ambio.asp>. 3 pages. (Year: 2008).*

Okto Ophtho. "AnnbioDry2™ Human Amniotitic Membrane Allograft". Internet archive date: Aug. 21, 2008. [Retrieved from the Internet on: Aug. 31, 2018]. Retrieved from: <URL: https://web.archive.org/web/20080821120552/http://www.oktoophtho.com/eyecare/ambio.asp>. 1 page. (Year: 2008).*

AmbioDisk™. 2 pages. (Year: 2012).*

Lim et al. "Biological and Ultrastructural Properties of Acelagraft, a Freeze-Dried .gamma.-Irradiated Human Amniotic Membrane". Arch Ophthalmolnol 128 (No. 10), pp. 1303-1310 (Year: 2010).*

* cited by examiner

*Primary Examiner* — Amy L Clark
(74) *Attorney, Agent, or Firm* — Barnes & Thornburg LLP (57) ABSTRACT

An ocular covering fabricated from at least one amniotic membrane, at least one chorionic membrane, or at least one amniotic membrane and at least one chorionic membrane obtained from human birth tissue is provided. Methods of preparing the one or more membranes to form an ocular covering are provided. Methods of treating a disease, condition, or surgical site of the eye and surrounding tissue are also provided.

3 Claims, 2 Drawing Sheets

OCULAR COVERING AND METHOD OF USE

CROSS-REFERENCE TO RELATED APPLICATION

The present application claims the benefit of priority to U.S. Provisional Application No. 61/757,862 filed Jan. 29, 2013, the contents of which is herein incorporated by reference in its entirety.

FIELD OF THE INVENTION

The present invention is directed to a human birth tissue construct, as well as methods of processing human birth tissue to prepare an ocular covering and methods of using the same for the treatment of ocular diseases and conditions as well as for the regeneration or repair of cells and tissues of and around the eye.

BACKGROUND OF THE INVENTION

Human placental tissue has been used for over a century in various surgical procedures, including skin transplantation and wound surface disorders. The tissue has been shown to provide good wound protection, prevent surgical adhesions, reduce pain, reduce wound dehydration, and provide anti-inflammatory and anti-microbial effects.

The placenta is a fetomaternal organ consisting of a placental globe, umbilical cord, umbilical cord blood, associated membranes (chorionic membrane and amniotic membrane), amniotic fluid and other gelatins, fluids, cells and extracellular material. The chorionic membrane and the amniotic membrane are attached by loose connective tissue and make up the placental sac. The innermost membrane of the placental sac is the amniotic membrane, which comes into contact with the amniotic fluid that surrounds the fetus. The amniotic membrane is avascular and lined by simple columnar epithelium overlying a basal membrane. The chorionic membrane is the outermost layer of the sac and is heavily cellularized. The placental membranes have an abundant source of collagen that provides an extracellular matrix to act as a natural scaffold for cellular attachment in the body. Collagen provides a structural tissue matrix that facilitates, among other things, cell migration and proliferation in vivo.

Various manufacturing processes have been employed to create ocular coverings composed of human birth tissue material that, when applied to the eye or surrounding ocular tissue, require a support material, tissue glue/adhesive or sutures to hold the covering in place. However, use of each of these products poses individualized problems. For example, use of suture to hold an ocular covering in place often causes side effects, including granuloma formation, tissue necrosis and stitch abscess. Use of an adhesive to hold an ocular covering in place is challenging to the clinician in that adhesives have a tendency to spread to undesired areas, causing pain or even possibly gluing the eyelid shut. Support materials such as those disclosed in U.S. Pat. No. 7,494,802, may irritate the eye or may be dislocated by eye blinking. Thus, there remains a need for an ocular covering composed of human birth tissue that is uniquely processed to allow adhesion to the eye without the aid of support materials, tissue glue/adhesives or sutures and is used to treat various ocular diseases and conditions as well as aid in the regeneration or repair of cells and tissues of the eye.

SUMMARY OF THE INVENTION

The present invention is generally directed to an ocular covering composed of human birth tissue, processes for producing the covering and uses thereof. The ocular covering of the present invention has unique properties that prevent fibrous scar formation, aid in treatment of ocular diseases, and aid in the regeneration or repair of cells and tissues of the eye when the covering is placed on an area of the eye or otherwise applied postoperatively after a variety of surgical procedures. The ocular covering is particularly suited to aid in healing, including pain reduction, scar minimization, and decreased inflammation. The ocular covering as described herein is processed in a manner such that the resulting ocular covering does not require the aid of support materials, tissue glue/adhesives or sutures to adhere to the eye or surrounding tissue.

According to one aspect, an ocular covering is provided that includes at least one amniotic membrane, or at least one chorionic membrane, or at least one amniotic membrane and at least one chorionic membrane. The membrane(s) is/are treated with at least one alcohol composition followed by terminal sterilization to form an ocular covering. The alcohol composition comprises from about 90% to about 100% ethanol. Terminal sterilization is carried out via gamma irradiation or electron beam irradiation.

According to another aspect, a method of preparing a membrane for an ocular covering is provided. The method includes the steps of:

(a) obtaining amniotic membrane, chorionic membrane, or both amniotic and chorionic membrane from a seronegative, healthy human via Cesarean section or vaginal delivery;

(b) immersing the membrane in a basin containing a sterile saline solution;

(c) agitating the basin to liberate excess blood and fluids from the membrane;

(d) rinsing the membrane with a sterile saline solution;

(e) covering the membrane with a substrate on both the fetal membrane side and the maternal membrane side;

(f) optionally, immersing the membrane in an alcohol composition;

(g) optionally, rinsing the membrane with a sterile saline solution;

(h) optionally, soaking the membrane in a sterile saline solution;

(i) immersing the membrane in an alcohol composition for a period of from about 24 hours to about 384 hours;

(j) removing the substrate from both the fetal membrane side and the maternal membrane side;

(k) spreading the membrane on a flat, dry and sterile surface;

(l) allowing the membrane to air dry completely at ambient temperature for a period of up to three hours;

(m) cutting the membrane to a predetermined size; and (n) placing the fetal side of the membrane directly onto a pre-cut substrate to form an ocular covering.

The method of preparing a membrane for an ocular covering may further include the steps of packaging the ocular covering in a dry state and terminally sterilizing the packaged ocular covering using irradiation. According to one embodiment, the method may further include the step of removing the chorionic membrane via blunt dissection and discarding the chorionic membrane. According to another embodiment, the method may further include the step of placing the membrane in sterile saline solution for a period of up to about five days between steps (a) and (b). In such an embodiment, the sterile saline solution includes from about 0.9% to about 20% NaCl. According to one embodiment, the sterile saline solution in step (b) may include from about 0.9% to about 20% NaCl. According to one embodiment, the sterile saline solution in steps (d) and (g) may also include from about 0.9% to about 20% NaCl. According to one embodiment, the rinse steps (d) and (g) are conducted for a maximum time period of five minutes. According to one embodiment, the sterile saline solution in step (h) comprises from about 0.9% to about 20% NaCl, and the soak in step (h) is conducted for a maximum period of about 35 minutes. According to one embodiment, the alcohol composition in steps (f) and (i) each include from about 90% to about 100% ethanol. According to another embodiment, the alcohol composition in steps (f) and (i) includes 95.5% ethanol. According to another embodiment, the alcohol composition in steps (f) and (i) includes 100% ethanol. According to one embodiment, the method further includes the step of treating the membrane with an oxidizer between steps (a) and (b). According to one embodiment, the oxidizer is hydrogen peroxide. According to such an embodiment, the step of treating the membrane further includes the steps of:

(a) rinsing the membrane with about 120 ml of sterile isotonic solution per gram of membrane for a time period of up to about ten minutes;

(b) treating the membrane with about 60 ml of hydrogen peroxide per gram of membrane for a time period of up to about ten minutes; and (c) rinsing the membrane with about 120 ml of sterile isotonic solution per gram of membrane for a time period of up to about ten minutes.

According to another aspect, an ocular covering is provided that is produced by the aforementioned method. According to one embodiment, an ocular covering is provided that is produced by the aforementioned method, whereby the ethanol residual levels determined by gas chromatography are not detected at the corresponding minimum report limit.

According to another aspect, a method of treating an ocular disease or condition is provided. The method of treating an ocular disease or condition includes the steps of preparing an ocular covering as provided herein and placing the ocular covering on or around at least a portion of an eye or a tissue surrounding an eye. According to one embodiment, the ocular covering is hydrated prior to placement.

According to another aspect, a method of treating an ocular surgical site is provided. The method of treating an ocular surgical site includes the steps of preparing an ocular covering as provided herein and placing the ocular covering on or around at least a portion of an eye or a tissue surrounding an eye subject to an ocular surgical procedure. According to one embodiment, the surgical procedure is glaucoma surgery, cataract surgery, corneal surgery, vitreoretinal surgery, eye muscle surgery, oculoplastic surgery or an ocular surgical procedure that involves a structure of an eye or tissue adjacent to an eye.

According to another aspect, a kit for use by an ophthalmologic professional is provided. According to one embodiment, the kit includes one or more packaged and sterilized ocular coverings as provided herein. The kit may further include at least one set of instructions. The kit may optionally include at least one composition or device for delivering, fastening or fixing the ocular covering on or around the eye or tissue surrounding the eye.

According to another aspect, a method of treating dry eye symptoms or chronic dry eye disease is provided. The method comprises the steps of preparing the ocular covering by the aforementioned method(s); placing the ocular covering on or around a portion of an eye or tissue surrounding an eye; and optionally, securing the ocular covering with a composition or device for fastening or fixing the ocular covering on or around the eye.

According to another aspect, a method for treating pain and/or inflammation of the eye is provided. The method comprises the steps of preparing the ocular covering by the aforementioned method(s); placing the ocular covering on or around a portion of an eye or tissue surrounding an eye; and optionally, securing the ocular covering with a composition or device for fastening or fixing the ocular covering on or around the eye.

DETAILED DESCRIPTION OF THE INVENTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise. As used in the specification, and in the appended claims, the words "optional" or "optionally" mean that the subsequently described event or circumstance can or cannot occur. For example, the phrase "optionally soaking the membrane" means that the soaking step may or may not be performed.

The present invention generally relates to an ocular covering that is prepared from human birth tissue. As used herein, the term "human birth tissue" includes, but is not limited to, elements of the placental organ such as, for example, the placental globe, umbilical cord, associated membranes (chorionic membrane and amniotic membrane), other gelatins, fluids, cells and extracellular material obtained from a seronegative, healthy human. As used herein, the term "covering" refers to a patch, graft, or other material embodiment suitable for contacting the eye or surrounding tissue. As used to herein, the term "ocular covering" refers to a construct that is applied onto or around an area of the eye or tissue surrounding the eye.

In particular, the invention relates to the use of amniotic membrane, chorionic membrane, or a combination of amniotic and chorionic membranes obtained from human birth tissue to form an ocular covering. The invention further relates to methods for aseptically processing intact amnion and/or chorion membranes to produce a material that may be used to prepare an ocular covering.

The amniotic and chorionic membranes may be utilized alone or in various combinations or layers to form the ocular covering. The present disclosure provides methods of preparing an ocular covering that includes an amniotic membrane, a chorionic membrane, or both a chorionic and an amniotic membrane. Thus, the term "membrane" refers to an amniotic membrane, a chorionic membrane, or both a chorionic and an amniotic membrane. According to one embodiment, the ocular covering includes one or more layers including an amniotic membrane. According to another embodiment, the ocular covering includes one or more layers that include a chorionic membrane. According to yet another embodiment, the ocular covering includes one or more layers of an amniotic membrane and one or more layers of a chorionic membrane.

According to one embodiment, the ocular covering includes at least one amniotic membrane, or at least one chorionic membrane, or at least one amniotic membrane and at least one chorionic membrane. In such an embodiment, the membrane(s) is/are not cross-linked. The membrane(s) is/are treated with at least one alcohol composition that includes typically from about 90% to about 100% ethanol. The resulting membrane(s) is/are terminally sterilized to form an ocular covering.

To obtain human birth tissue material, potential human birth tissue donors providing informed consent are pre-screened during an examination of pre-natal medical records and blood test results. A comprehensive medical history and behavior risk assessment is obtained from the donor prior to donation incorporating U.S. Public Health Service guidelines. Discussions with the physician(s) and/or the donor mother are conducted to identify circumstances that may lead to the exclusion of the donor or donated tissue. Additionally, a physical exam is performed on the donor to determine whether there is evidence of high risk behavior or infection and to determine the overall general health of the donor.

Infectious disease testing of donor blood specimens is performed for each tissue donor on a specimen collected at the time of donation or within seven days prior to or after donation. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc-total, meaning IgG and IgM); antibodies to the hepatitis C virus (anti-HCV); NAT for HCV; antibodies to human T-lymphotropic virus type I and type II (anti-HTLV-I and anti-HTLV-II); and syphilis (a non-treponemal or treponemal-specific assay may be performed).

Human birth tissue is preferably recovered from a full-term aseptic Cesarean delivery of a newborn. Alternatively, human birth tissue is recovered from a full-term vaginal delivery of a newborn. The placental organ, including the placental globe, umbilical cord, associated membranes (chorionic membrane and amniotic membrane), other gelatins, fluids, cells and extracellular matrix can be recovered from a seronegative, healthy human after the newborn is removed. The placental globe, umbilical cord, other gelatins, fluids, cells and extracellular matrix can be removed and discarded.

The membrane(s) giving rise to the ocular covering as described herein may be produced by processing human birth tissue according to the steps provided herein. Processing does not change the physical properties of the resulting membrane so as to yield the membrane tissue unacceptable for clinical use. Instruments, solutions, and supplies coming into contact with tissue during the processing of the placental tissue are sterile. All surfaces coming in contact with tissue intended for transplant are either sterile or draped using aseptic technique.

Throughout processing, the orientation of the particular membrane is identified to ensure that in use, the correct side of the membrane is placed on or around a portion of the eye or tissue surrounding the eye. Either the fetal side or the maternal side of the membrane may be placed on or around a portion of the eye or tissue surrounding the eye, depending upon the specific use or procedure that is being performed.

Figure 1:
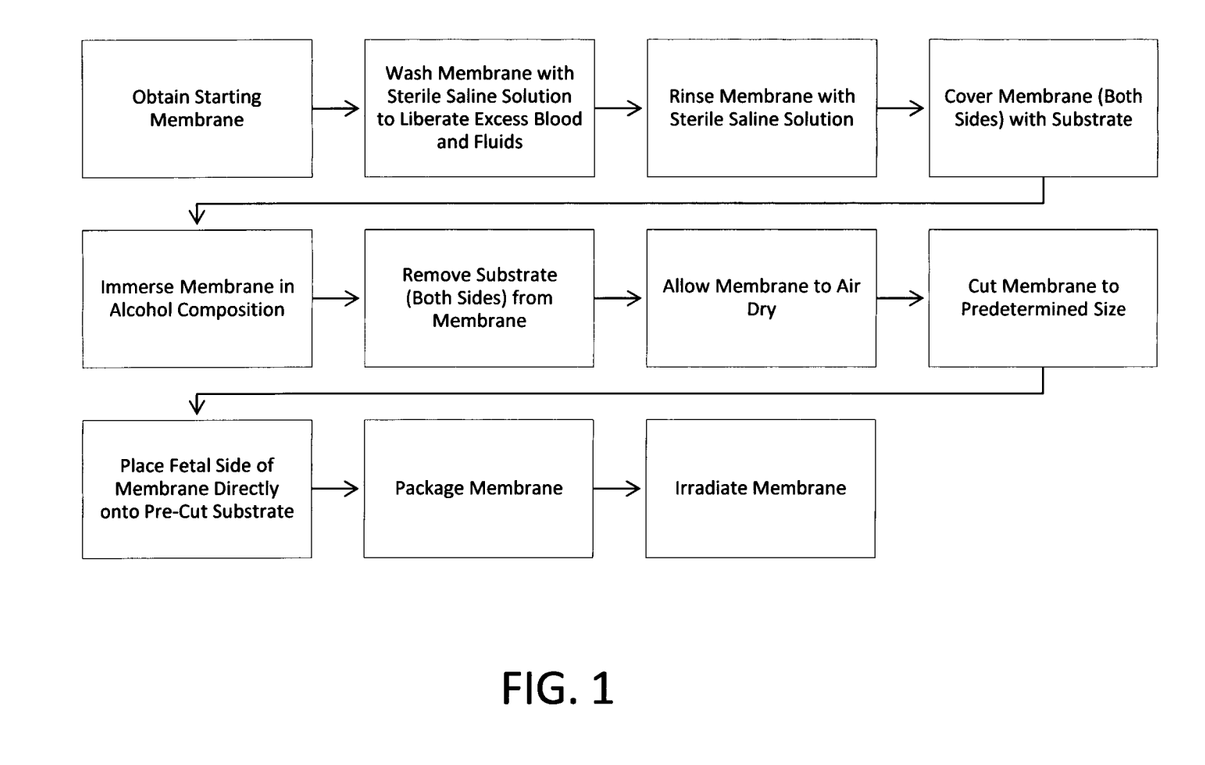
FIG. 1 illustrates a method of preparing an ocular covering according to one embodiment.
Figure 2:
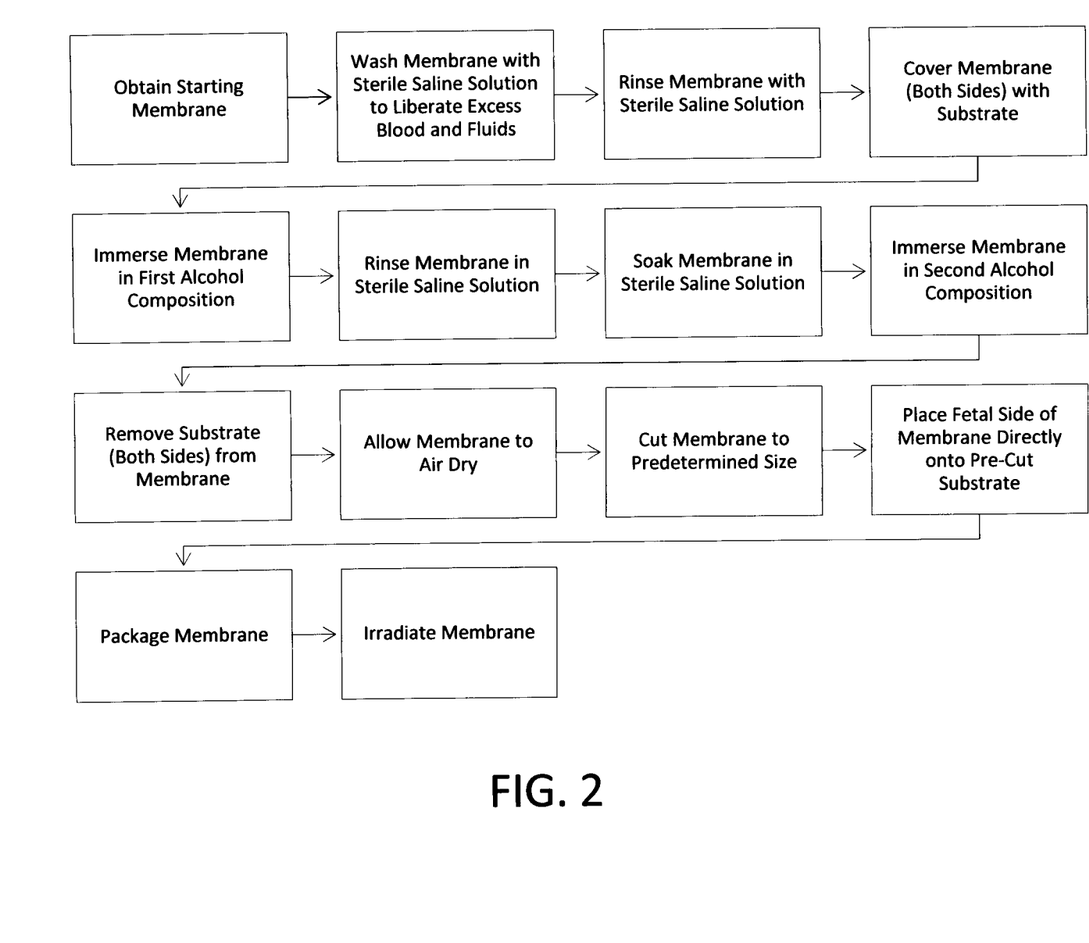
FIG. 2 illustrates a method of preparing an ocular covering according to one embodiment.

According to the embodiment as illustrated in FIG. 1 or FIG. 2, the ocular covering is prepared by first obtaining amniotic membrane, chorionic membrane, or both amniotic and chorionic membrane from a seronegative, healthy human via cesarean section or vaginal delivery as described herein. In particular embodiments where only the amniotic membrane is chosen for further processing, the chorionic membrane can be removed by blunt dissection. For example, the chorionic membrane may be removed by applying finger pressure and sliding it off of the amniotic membrane using as little pressure as possible to avoid tearing of the amnion. The chorionic membrane and any excess tissue can be discarded.

The recovered amniotic membrane, chorionic membrane, or both amniotic and chorionic membrane may be initially stored in a sterile saline solution at a temperature between about 1° C. to about 10° C. for a period of up to about five days prior to further processing. According to one embodiment, the sterile saline solution comprises from about 0.09% to about 20% NaCl, preferably 15% NaCl.

Optionally, the membrane(s) may be treated with an oxidizer. In one embodiment, the oxidizer is hydrogen peroxide, which is also used as a sterilant and to enhance the solubilization of lipids. Such a treatment process includes the steps of:

(a) rinsing the membrane with 120 ml of sterile isotonic solution per gram of membrane for a period of up to about ten minutes;

(b) treating the membrane with 60 ml of hydrogen peroxide per gram of membrane for a period of up to about ten minutes; and (c) rinsing the membrane with 120 ml of sterile isotonic solution per gram of membrane for a period of up to about ten minutes.

The membrane is then immersed in a basin containing a sterile saline solution. According to one embodiment, the sterile saline solution includes typically from about 0.9% to about 20% NaCl.

Excess blood and fluids may be liberated from the membrane by gently stirring or swirling the fluid in a circular motion in the basin or by placing the basin on a shaker. The membrane can then be rinsed with a sterile saline solution. In one embodiment, the sterile saline solution includes NaCl in a concentration range of about 0.9% to about 20%. In one embodiment, the membrane may be rinsed in bowls or trays of sufficient size to allow the membrane to be spread out to improve the rinse coverage. Sufficient saline solution is utilized to ensure that the membrane is completely immersed. The saline is then decanted into a discard basin.

Multiple saline rinse cycles may be performed. In one embodiment, the membrane is rinsed for two or more separate rinse cycles, with each rinse cycle lasting for a maximum of five minutes. The membrane is covered with a substrate on both the fetal membrane side and the maternal membrane side. Appropriate substrates include, but are not limited to, sterile mesh or polymer mesh of adequate size and shape for covering each side of the membrane.

According to the alternative embodiment as illustrated in FIG. 2, the membrane may optionally be immersed in an alcohol composition from about 90% to about 100% ethanol (see FIG. 2—referred to as "first alcohol composition"). In a preferred embodiment, the alcohol composition includes about 95.5% ethanol. In a preferred embodiment, the alcohol composition includes about 100% ethanol. An ocular covering produced according to the embodiment of FIG. 2 may be resorbed by the body and is particularly useful for eye tissue remodeling and aiding in the healing cascade.

As illustrated in the embodiment of FIG. 2, the membrane is then optionally rinsed with a sterile saline solution. Alternatively, the membrane is rinsed multiple times with a sterile saline solution. According to one embodiment, the sterile saline solution includes typically from about 0.9% to about 20% of NaCl. According to one embodiment, the rinse step is conducted for a maximum time period of five minutes. The membrane can then be optionally soaked in a sterile saline solution. According to one embodiment, the sterile saline solution includes typically from about 0.9% to about 20% of NaCl. According to one embodiment, soaking is conducted for a maximum period of about 35 minutes.

As illustrated in each of the embodiments of FIGS. 1 and 2, the membrane is then immersed in an alcohol composition for a period of typically from about 24 hours to about 384 hours. The alcohol composition includes about 90% to about 100% ethanol. In a preferred embodiment, the alcohol composition includes about 95.5% ethanol. In a preferred embodiment, the alcohol composition includes about 100% ethanol. Treatment of the membrane within a particular alcohol concentration range for the particular timeframe at this step in the process has yielded unexpected results related to the handling characteristics. One of ordinary skill in the art appreciates the difficulty of handling and manipulating amniotic and chorionic tissue when applied to a surgical site. Specifically, existing amniotic and chorionic grafts are difficult to place over a specific site, particularly because these grafts fold back over on themselves ("wrinkling"), rendering proper placement and positioning of the graft at the wound site very challenging. When treated with the aforementioned alcohol composition for the particular timeframe, the resulting ocular covering exhibits improved handling characteristics in that it does not "wrinkle" and allows for easy placement at the ocular site. Additionally, the membrane is uniquely processed to allow adhesion to the eye without the aid of support materials, tissue glue/adhesives or sutures. Furthermore, the alcohol treatment is multifunctional, providing a means of sterilization, preservation, and chemical dehydration for the membrane, in addition to serving as a radioprotectant for the membrane prior to terminal irradiation.

The substrate can then be removed from both the fetal membrane side and the maternal membrane side. The membrane can then be spread on a flat, dry and sterile surface. The membrane is then allowed to air dry completely at ambient temperature for a period of up to typically about three hours. The membrane can then be cut to the desired size, covered with a substrate, and subsequently packaged. The ocular covering can be cut into patches of any desired size for a particular application by a rotary type cutting tool. A grooved or similarly indicated cutting board may be used to aid in cutting a straight and correctly sized covering. In another embodiment, the ocular covering is cut by free hand using a scalpel and ruler to achieve the desired size. In another embodiment, the ocular covering can be cut using an ocular trephine. The fetal side of the membrane can then be placed directly onto a pre-cut substrate to form an ocular covering. Suitable substrates include, for example, a gauze or synthetic mesh. Preferably, the ocular covering is packaged in a dry state. The covering can be removed after the opposing side has been applied to the surgical site. The packaging and covering as disclosed herein can facilitate the handling of the ocular covering, namely maintaining and identifying the orientation of the fetal and maternal side of the ocular covering for the user. The packaging may also promote storage of the ocular covering.

The packaged ocular covering can be terminally sterilized using irradiation. In one embodiment, an electron beam irradiation is applied in an amount up to about 45 kGy. The sterilized ocular covering may be stored for up to typically about two years from the date of processing. In one embodiment, the ocular covering may be stored under proper conditions for as much as about five years following processing. The sterilized ocular covering may be stored in any container suitable for long-term storage. Preferably, the sterilized ocular covering is stored in a sterile double peel-pouch package.

The ocular covering as described herein may be of various sizes, thicknesses, and shapes. The ocular covering is preferably of sufficient size and shape to be applied onto or around an eye or tissue surrounding the eye. The ocular covering may be any shape or conformation that facilitates the treatment of a portion of the eye or tissue surrounding the eye, including ocular or facial surgery, or the treatment or repair of a discontinuity or trauma in the eye, eyelid, or surrounding tissues. In certain embodiments, the ocular covering may be shaped as a square, rectangular, circular or oval, or may be cut to conform generally to the shape of an eye, eye muscle, eyelid, or other surrounding tissue. The thickness of the ocular covering may vary depending on application, the type of membrane and the number of membrane layers. Typically, the ocular covering is from about 0.01 mm to about 0.35 mm thick.

A method of treating an ocular disease or condition is also provided. The method of treating an ocular disease or condition includes the steps of preparing an ocular covering as provided herein and placing the ocular covering on or around at least one eye or tissue surrounding the eye. The ocular covering as provided herein may be used to treat a variety of ocular diseases and conditions. Exemplary diseases and conditions include, but are not limited to, FUCHS dystrophy and other corneal dystrophies, conjunctivitis, corneal infections, Iridocorneal Endothelial Syndrome, ocular herpes, macular edema, bullous keratopathy, retinitis pigmentosa, dry eye, chronic dry eye disease, allergic conjunctivitis, scleritis, uveitis, neuritis, pemphigus, Sjögren's syndrome, Behcet's syndrome, toxoplasmosis, Birdshot choroidopathy, papillitis, venous occlusions, retinal detachment, ocular ischemia and trauma, ocular histoplasmosis syndrome, myopic degeneration, angioid streaks, idiopathic central serous chorioretinopathy, inflammatory conditions of the retina and or choroid, age-related macular degeneration, diabetic and other retinopathies, glaucoma and other optic neuropathies, corneal defects, neurtrophic corneal ulcers, conjunctival surface reconstruction, conjunctivochalasis, pterygium, chemical burns, thermal burns, Stevens Johnson Syndrome, pars planitis, sarcoidosis, sympathetic ophthalmia, serpiginous choroidopathy, diffuse pigment epitheliopathy, Vogt-Koyanagi syndrome, polyarteritis nodosa, symblepharon and other ocular surface conditions.

A method of treating an ocular surgical site is also provided. The method of treating an ocular surgical site includes the steps of preparing an ocular covering as provided herein and placing the ocular covering on or around at least one eye or tissue surrounding an eye subject to an ocular surgical procedure. The ocular covering may act to reduce post-operative scar tissue formation, reduce pain, reduce inflammation, and, generally, aid in the healing cascade.

According to one embodiment, the surgical procedure is glaucoma surgery, cataract surgery, corneal surgery, vitreoretinal surgery, eye muscle surgery, oculoplastic surgery or an ocular surgical procedure that involves a structure of an eye or tissue adjacent to an eye. In certain embodiments, the glaucoma surgery is trebeculoplasty, iridotomy, iridactomy, a filtering surgery, anterior sclerotomy, sclerostomy, penetrating trabeculotomy, non-penetrating trabeculotomy, trepanotrabeculectomy, goniotomy, cyclotomy, cycloanemization, cyclocryotherapy, cyclocryopexy, iridenclesis, iridocyclectomy, iridosclerotomy, corenclisis, goniocurretage or leaking filtering blebs following glaucoma surgery. In certain embodiments, the surgery is the phacoemulsification of a cataract in the eye. Other ocular surgical procedures include repair of a phacoemulsification burn, a trabulectomy, implantation of an orbital implant, ciliarotomy, ciliectomy, ciliotomy, corectomedialysis, corectomy, corelysis, coremorphosis, coreplasty, coreoplasty, pupillomydriasis, cyclectomy, cyclectomy, iridectomesodialysis, iridodialysis, iridesis or iridocorneosclerectomy. According to another embodiment, the ocular surgical procedure changes the shape of the cornea or is a refractive surgery. According to another embodiment, the ocular surgical procedure is for correcting keratoconus. In certain embodiments, the ocular surgical procedure is photorefractive keratectomy (PRK), laser-assisted sub-epithelial keratectomy (LASEK) or laser-assisted in situ keratomileusis (LASIK). In other emboidments, the ocular surgical procedure is automated lamellar keratoplasty (ALK), laser thermal keratoplasty (LTK), or conductive keratoplasty (CK). According to another embodiment, the ocular surgical procedure is a vitreoretinal surgery such as, for example, an anterior vitrectomy, pars plana vitrectomy, ignipuncture, macular hole repair, partial lamellar scierouvectomy, or posterior sclerotomy. According to another embodiment, the ocular surgical procedure is retinal surgery. According to another embodiment, the ocular surgical procedure is surgery to correct, repair or ameliorate trauma to the eye (e.g., trauma caused by, or associated with, a discontinuity in the eye). The trauma may be caused outside a surgical context (e.g., accident related). According to another embodiment, the ocular surgical procedure is an eye muscle surgery. According to another embodiment, the ocular surgical procedure is an oculoplastic surgery such as, for example, browplasty, eyelid reconstruction, blepharoplasty, ectropion repair, entropion repair, canthal resection, canthectomy, cantholysis, canthopexy, canthoplasty, canthorrhapy, canthotomy, canaliculodacryocystostomy, canaliculotomy, dacryoadenectomy, dacryocystectomy, dacryocystorhiostomy, dacryocystostomy, enucleation of the eye, evisceration, exenteration, or repair of an exposed orbital implant. According to another embodiment, the ocular surgical procedure is corneal surgery.

According to one embodiment, the length of time the ocular covering will remain on or around the eye or tissue surrounding the eye depends on the type of surgery, disease or condition subject to treatment. According to one embodiment, the ocular covering as described herein may replace tissue on or around an eye surface such that the ocular covering naturally becomes part of the eye as the eye heals or recovers. Alternatively, the ocular covering may cover the surface of an eye and subsequently be resorbed or dissolved while the eye heals or recovers. According to another embodiment, the ocular covering may be removed after healing and/or recovery.

If desired, the one or more membranes forming the ocular covering utilized in the methods provided herein may be treated, coated or impregnated with one or more of a variety of optional components to aid in disease resolution, healing, and recovery. Exemplary optional components include, but are not limited to, antibiotics, anti-inflammatory agents, anti-viral agents, growth factors, antiproliferative agents, cytokines, antihistamines, pain medications, biocides, cellular attractant and scaffolding reagents, wound healing agents or sealants, nutritional agents (e.g., vitamins), hormones, alkylating agents, immunomodulatory agents (e.g., steroids), and/or other specialized proteins or small molecules. The one or more membranes forming the ocular covering may be combined with a substrate (sterile gauze, sterile polymer material, sterile contact lens or other tissue or biomaterial) to increase the strength of the ocular covering.

If desired, the one or more membranes forming the ocular covering may be utilized with at least one composition or device for delivering, fastening or fixing the ocular covering on or around an eye or tissue surrounding an eye. Exemplary compositions include, but are not limited to, tissue glue or tissue adhesive, fibrin glue, fibrinogen glue, hydrogel tissue glue, chondroitin sulfate aldehyde, or natural proteins. Exemplary devices include, but are not limited to, sutures or forceps.

A kit for use by an ophthalmologic professional is also provided. According to one embodiment, the kit includes one or more packaged and sterilized ocular coverings as provided herein. The kit may further include at least on set of instructions. The kit may optionally include at least one composition or device for delivering, fastening or fixing the ocular covering on or around the eye or tissue surrounding the eye. Exemplary compositions include, but are not limited to, tissue glue or tissue adhesive, fibrin glue, fibrinogen glue, a hydrogel tissue glue, chondroitin sulfate aldehyde, or natural proteins. Exemplary devices include, but are not limited to, sutures or forceps. The kit may further include a container adapted to accommodate the aforementioned components while preserving the ocular covering as per applicable Food and Drug Administration guidelines.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

Having generally described the present invention, a further understanding can be obtained by reference to the examples provided herein for purposes of illustration only and are not intended to be limiting.

Example 1

The following example demonstrates one method of using an ocular covering for treatment of a defect resulting from pterygium removal. Pterygium is a benign growth that usually grows from the nasal side of the sclera and is characterized by elastotic degeneration of collagen and fibrovascular proliferation. Pterygia can range from small inactive lesions to large and aggressive lesions that can cause discomfort, obscured vision and corneal scarring.

The ocular covering was prepared according to the method of FIG. 1. Human birth tissue was obtained from a seronegative healthy mother via Cesarean section. To maximize the overall quality of the donated tissue, a recovery technician was present in the operating room during the donor's Cesarean section to assist the physician with recovery, treatment and handling of the birth tissue. The donor was surgically prepped and draped per AORN standards prior to the Cesarean section procedure. The recovery technician prepared the recovery site by establishing a sterile field on a back table in the operating room. Following delivery of the baby, the physician's assistant placed the human birth tissue en-bloc into a sterile basin. Maintaining sterility, the basin was transferred to the recovery technician onto the sterile field. Beginning at the amnion/chorion membrane surgical incision site, the recovery technician used blunt dissection to separate the chorionic membrane from the amniotic membrane, using care not to tear the amniotic tissue. The recovery technician then removed the amniotic membrane from the placental face until reaching the umbilical cord. At the site where the amnion is attached to the umbilical cord, the recovery technician dissected the amnion from the umbilical cord by making an incision in the amnion around the circumference of the umbilical cord. The amniotic membrane was transferred to a sterile container and rinsed with sterile saline to remove any blood or debris.

After thorough rinsing, the amniotic membrane was transferred into a sterile bag and swab cultures were performed. Approximately 300 ml of transport solution (15% NaCl) was added to the sterile bag containing the recovered amniotic membrane. The bag was secured with a knot. The single-bagged amniotic membrane was then placed into a second sterile bag, which was securely knotted. The double-bagged amniotic membrane was then transferred into a plastic transport container to which the appropriate identification was affixed. The plastic transport container was placed in a qualified shipping container with an appropriate amount of wet ice to maintain refrigerated temperatures. The validated box arrived at the processing facility approximately one hour following recovery and was immediately placed in refrigerated temperatures (1-10° C.) and inspected per standard operating procedures.

Processing was performed on a sterile field using aseptic technique in a validated cleanroom at the processing facility. All manufacturing steps were recorded concurrently by a circulating technician on a designated processing record. The amniotic membrane was removed from the plastic transport container and outer bag. The inner bag containing the amniotic membrane was aseptically passed onto a sterile field. The amniotic membrane was transferred to a sterile basin where any residual blood was rinsed away with a sterile saline solution (0.9% NaCl). The amniotic membrane was placed maternal side up onto a sterile cutting board. The membrane was inspected for any damage or debris. Any stringy ends were cut away. Keeping the membrane flat on the sterile cutting board, the amnion was rinsed with a sterile saline solution (0.9% NaCl). The maternal side of the membrane was covered with sterile mesh, allowing the mesh to slightly overlap the membrane. The membrane was gently lifted, positioned fetal side up, and placed back on the sterile cutting board, using caution to not disturb the mesh/amnion interface. The fetal side of the membrane was rinsed with a sterile saline solution (0.9% NaCl). Then, the fetal side of the membrane was covered with sterile mesh, allowing the mesh to slightly overlap the membrane. The mesh/membrane/mesh was transferred into a sterile basin, maternal side down, unfolded and flat, using caution not to disturb the mesh/amnion interface. 1 L of 95.5% ethanol solution was added to the sterile basin, fully immersing the mesh/membrane/mesh interface and the basin was re-covered. The sterile basin was placed inside a sterile bag and transferred to a quarantine refrigerator. The mesh/membrane/mesh interface remained in the 1 L of 95.5% ethanol solution for 25 hours.

A sterile field was established in a validated cleanroom at the processing facility. All manufacturing steps were recorded concurrently by a circulating technician on a designated processing record. The sterile bag containing the sterile basin was removed from the quarantine refrigerator. The sterile basin was removed from the sterile bag and aseptically transferred to the sterile work area in the cleanroom. The mesh/membrane/mesh interface was removed from the 95.5% ethanol solution and placed maternal side down on a sterile cutting board. The mesh was removed from the fetal side of the membrane. The membrane/mesh was carefully flipped, and the mesh was removed from the maternal side of the membrane. The membrane was repositioned onto the cutting board in a completely flat position. The membrane was allowed to dry for five (5) minutes. Using a rotary cutting blade, the membrane was sectioned into product sizes, in accordance with the processing plan. The dry membrane grafts were carefully loosened from the cutting board and placed onto pre-cut sections of mesh with the maternal side of each membrane graft orienting up and the fetal side to the mesh. Each individual tissue patch was packaged into a sterile foil inner pouch using aseptic technique. Using an AccuSeal 540Plus sealer, each foil pouch was sealed inside a Tyvek pouch following standard operating procedures. Each Tyvek pouch was assigned and labeled with a tissue identification number, designed to ensure the traceability of tissue from receipt through clinical use, transfer or destruction. Each unit was terminally sterilized via E Beam irradiation at 25.5-27.5 kGy.

The patient was a 44 year old male with a pterygium in the right eye. The patient was treated with aggressive eye drops and ointment therapies for several months with no evidence of healing. The patient presented with severe discomfort in a follow-up visit, and it was confirmed that the pterygium was approaching the visual axis. Pterygium removal was performed and the conjunctival edges were undermined approximately 1.5 mm. The ocular covering was place over the defect and inserted under the conjunctival edges. The ocular covering adhered to both the conjunctiva and the sclera. As such, no surgical glue or sutures were used to fasten the graft to the structures of the eye.

At one week post-op, the wound covering had completely incorporated into the defect, the defect appeared to be healed, and the patient reported being pain-free. At six weeks post-op, the ophthalmologist determined that the defect was resolved, and the patient was released with no further follow-up action required.

Example 2

The following example demonstrates one method of using an ocular covering to treat a patient with Anterior Basement Membrane Dystrophy (ABMD) and Subsequent Recurrent Corneal Erosions (RCE). The wound covering was prepared according to the method of FIG. 1 and processed according to the methods described particularly in Example 1.

A 57 year old female patient presented with ABMD and an associated RCE in the left eye. The patient was treated with aggressive lubrication therapies with no evidence of healing. Thereafter, the patient underwent a phototherapeutic keratectomy (PTK) for left eye corneal erosions. Seven months later, the erosions recurred, and the patient was treated with corneal tattooing. The patient returned to the clinic with subsequent erosions approximately 2.5 years later. Following epithelial debridement, a bandage contact lens was placed on the ocular surface. For approximately another 1.5 years, the patient was treated conservatively with lubricants but still experienced pain and non-healing of the erosions. For eleven months, the patient wore a new bandage contact lens weekly for the symptoms. The patient also used Restasis® for dry eye symptoms in both eyes for one year.

The ocular covering was placed on the ocular surface of the patient's left eye in the clinic setting. The ocular covering was applied without glue or suture; however, a bandage contact lens was placed topically over the wound covering.

On day one post-op, the patient reported no pain. On day five post-op, the wound covering had fully incorporated. Slit lamp microscopy demonstrated healing of the erosion. At two months post-op, the patient reported no pain, and no erosions had recurred. At three months post-op, the patient reported no pain, and no erosions had recurred. Additionally, while not expected, the patient reported that she had discontinued using Restasis® in her left eye as she no longer experienced dry eye symptoms.

Example 3

The following example demonstrates one method of using an ocular covering for treatment of a patient with a history of corneal dystrophy and severe keratitis sicca.

The ocular covering was prepared according to the method of FIG. 1. Human birth tissue was obtained from a seronegative healthy mother via Cesarean section. To maximize the overall quality of the donated tissue, a recovery technician was present in the operating room during the donor's Cesarean section to assist the physician with recovery, treatment and handling of the birth tissue. The donor was surgically prepped and draped per AORN standards prior to the Cesarean section procedure. The recovery technician prepared the recovery site by establishing a sterile field on a back table in the operating room. Following delivery of the baby, the physician's assistant placed the human birth tissue en-bloc into a sterile basin. Maintaining sterility, the basin was transferred to the recovery technician onto the sterile field. Beginning at the amnion/chorion membrane surgical incision site, the recovery technician used blunt dissection to separate the chorionic membrane from the amniotic membrane, using care not to tear the amniotic tissue. The recovery technician then removed the amniotic membrane from the placental face until reaching the umbilical cord. At the site where the amnion is attached to the umbilical cord, the recovery technician dissected the amnion from the umbilical cord by making an incision in the amnion around the circumference of the umbilical cord. The amniotic membrane was transferred to a sterile container and rinsed with sterile saline to remove any blood or debris.

After thorough rinsing, the amniotic membrane was transferred into a sterile bag and swab cultures were performed. Approximately 300 ml of transport solution (15% NaCl) was added to the sterile bag containing the recovered amniotic membrane. The bag was secured with a knot. The single-bagged amniotic membrane was then placed into a second sterile bag, which was securely knotted. The double-bagged amniotic membrane was then transferred into a plastic transport container to which the appropriate identification was affixed. The plastic transport container was placed in a qualified shipping container with an appropriate amount of wet ice to maintain refrigerated temperatures. The validated box arrived at the processing facility approximately one hour following recovery and was immediately placed in refrigerated temperatures (1-10° C.) and inspected per standard operating procedures.

Processing was performed on a sterile field using aseptic technique in a validated cleanroom at the processing facility. All manufacturing steps were recorded concurrently by a circulating technician on a designated processing record. The amniotic membrane was removed from the plastic transport container and outer bag. The inner bag containing the amniotic membrane was aseptically passed onto a sterile field. The amniotic membrane was transferred to a sterile basin where any residual blood was rinsed away with a sterile saline solution (0.9% NaCl). The amniotic membrane was placed maternal side up onto a sterile cutting board. The membrane was inspected for any damage or debris. Any stringy ends were cut away. Keeping the membrane flat on the sterile cutting board, the amnion was rinsed with a sterile saline solution (0.9% NaCl). The maternal side of the membrane was covered with sterile mesh, allowing the mesh to slightly overlap the membrane. The membrane was gently lifted, positioned fetal side up, and placed back on the sterile cutting board, using caution to not disturb the mesh/amnion interface. The fetal side of the membrane was rinsed with a sterile saline solution (0.9% NaCl). Then, the fetal side of the membrane was covered with sterile mesh, allowing the mesh to slightly overlap the membrane. The mesh/membrane/mesh was transferred into a sterile basin, maternal side down, unfolded and flat, using caution not to disturb the mesh/amnion interface. 1 L of 100% ethanol solution was added to the sterile basin, fully immersing the mesh/membrane/mesh interface and the basin was re-covered. The sterile basin was placed inside a sterile bag and transferred to a quarantine refrigerator. The mesh/membrane/mesh interface remained in the 1 L of 100% ethanol solution for 162 hours.

A sterile field was established in a validated cleanroom at the processing facility. All manufacturing steps were recorded concurrently by a circulating technician on a designated processing record. The sterile bag containing the sterile basin was removed from the quarantine refrigerator. The sterile basin was removed from the sterile bag and aseptically transferred to the sterile work area in the cleanroom. The mesh/membrane/mesh interface was removed from the 100% ethanol solution and placed maternal side down on a sterile cutting board. The mesh was removed from the fetal side of the membrane. The membrane/mesh was carefully flipped, and the mesh was removed from the maternal side of the membrane. The membrane was repositioned onto the cutting board in a completely flat position. The membrane was kept wet until placed in the final drying position. The membrane was allowed to dry for 22 minutes. Using a 15 mm trephine, the membrane was sectioned into product sizes, in accordance with the processing plan. The dry membrane grafts were carefully loosened from the cutting board and placed onto pre-cut sections of sponge with the maternal side of each membrane graft orienting up and the fetal side to the sponge. Each individual tissue patch was packaged into a sterile inner PETG tray using aseptic technique. Using a MedPack MB6×9 Tray sealer, each inner PETG tray was sealed inside an outer PETG tray following standard operating procedures. Each outer PETG tray was assigned and labeled with a tissue identification number, designed to ensure the traceability of tissue from receipt through clinical use, transfer or destruction. Each unit was terminally sterilized via E Beam irradiation at 28.0-30.1 kGy.

A 78 year old patient with a history of corneal dystrophy and chronic dry eye treated with bandage contact lenses presented with fulminant and diffuse keratitis with completely opacified cornea and light pain in the left eye. The left eye was swollen closed with some cloudy discharge. The bandage contact lens was removed and sent for culture, and topical antibiotics were initiated. Three days later, the left eye was examined and had developed an extensive corneal ulcer with a hypopyon. Lab results indicated *Pseudomonas* with sensitivity to Gentamycin. Gentamycin drops were prescribed. The patient returned for a follow-up appointment a week later. While the infection appeared to be controlled with the topical antibiotic application, re-epithelialization was hampered, yet necessary, for the survival of the cornea.

The ocular covering was applied to the cornea without glue or suture. A bandage contact lens was placed topically over the ocular covering. At one month post-application, the patient's epithelium was intact, and she reported zero pain or discomfort in the affected eye and stable vision. At two months post-application, the extensive corneal ulcer was healed and the patient reported zero pain or discomfort in the affected eye and stable vision.

Example 4

The following example demonstrates one method of using an ocular covering for treatment of a patient with a non-healing corneal persistent epithelial defect (PED). The ocular covering was prepared according to the method of FIG. 1. Human birth tissue was obtained from a seronegative healthy mother via Cesarean section. To maximize the overall quality of the donated tissue, a recovery technician was present in the operating room during the donor's Cesarean section to assist the physician with recovery, treatment and handling of the birth tissue. The donor was surgically prepped and draped per AORN standards prior to the Cesarean section procedure. The recovery technician prepared the recovery site by establishing a sterile field on a back table in the operating room. Following delivery of the baby, the physician's assistant placed the human birth tissue en-bloc into a sterile basin. Maintaining sterility, the basin was transferred to the recovery technician onto the sterile field. Beginning at the amnion/chorion membrane surgical incision site, the recovery technician used blunt dissection to separate the chorionic membrane from the amniotic membrane, using care not to tear the amniotic tissue. The recovery technician then removed the amniotic membrane from the placental face until reaching the umbilical cord. At the site where the amnion is attached to the umbilical cord, the recovery technician dissected the amnion from the umbilical cord by making an incision in the amnion around the circumference of the umbilical cord. The amniotic membrane was transferred to a sterile container and rinsed with sterile saline to remove any blood or debris.

After thorough rinsing, the amniotic membrane was transferred into a sterile bag and swab cultures were performed. Approximately 300 ml of transport solution (15% NaCl) was added to the sterile bag containing the recovered amniotic membrane. The bag was secured with a knot. The single-bagged amniotic membrane was then placed into a second sterile bag, which was securely knotted. The double-bagged amniotic membrane was then transferred into a plastic transport container to which the appropriate identification was affixed. The plastic transport container was placed in a qualified shipping container with an appropriate amount of wet ice to maintain refrigerated temperatures. The validated box arrived at the processing facility approximately one hour following recovery and was immediately placed in refrigerated temperatures (1-10° C.) and inspected per standard operating procedures.

Processing was performed on a sterile field using aseptic technique in a validated cleanroom at the processing facility. All manufacturing steps were recorded concurrently by a circulating technician on a designated processing record. The amniotic membrane was removed from the plastic transport container and outer bag. The inner bag containing the amniotic membrane was aseptically passed onto a sterile field. The amniotic membrane was transferred to a sterile basin where any residual blood was rinsed away with a sterile saline solution (0.9% NaCl). The amniotic membrane was placed maternal side up onto a sterile cutting board. The membrane was inspected for any damage or debris. Any stringy ends were cut away. Keeping the membrane flat on the sterile cutting board, the amnion was rinsed with a sterile saline solution (0.9% NaCl). The maternal side of the membrane was covered with sterile mesh, allowing the mesh to slightly overlap the membrane. The membrane was gently lifted, positioned fetal side up, and placed back on the sterile cutting board, using caution to not disturb the mesh/amnion interface. The fetal side of the membrane was rinsed with a sterile saline solution (0.9% NaCl). Then, the fetal side of the membrane was covered with sterile mesh, allowing the mesh to slightly overlap the membrane. The mesh/membrane/mesh was transferred into a sterile basin, maternal side down, unfolded and flat, using caution to not disturb the mesh/amnion interface. 1 L of 100% ethanol solution was added to the sterile basin, fully immersing the mesh/membrane/mesh interface and the basin was re-covered. The sterile basin was placed inside a sterile bag and transferred to a quarantine refrigerator. The mesh/membrane/mesh interface remained in the 1 L of 100% ethanol solution for 123.33 hours.

A sterile field was established in a validated cleanroom at the processing facility. All manufacturing steps were recorded concurrently by a circulating technician on a designated processing record. The sterile bag containing the sterile basin was removed from the quarantine refrigerator. The sterile basin was removed from the sterile bag and aseptically transferred to the sterile work area in the cleanroom. The mesh/membrane/mesh interface was removed from the 100% ethanol solution and placed maternal side down on a sterile cutting board. The mesh was removed from the fetal side of the membrane. The membrane/mesh was carefully flipped, and the mesh was removed from the maternal side of the membrane. The membrane was repositioned onto the cutting board in a completely flat position. The membrane was kept wet until placed in the final drying position. The membrane was allowed to dry for 22 minutes. Using a 12 mm trephine, the membrane was sectioned into product sizes, in accordance with the processing plan. The dry membrane grafts were carefully loosened from the cutting board and placed onto pre-cut sections of sponge with the maternal side of each membrane graft orienting up and the fetal side to the sponge. Each individual tissue patch was packaged into a sterile inner PETG tray using aseptic technique. Using a MedPack MB6×9 Tray sealer, each inner PETG tray was sealed inside an outer PETG tray following standard operating procedures. Each outer PETG tray was assigned and labeled with a tissue identification number, designed to ensure the traceability of tissue from receipt through clinical use, transfer or destruction. Each unit was terminally sterilized via E Beam irradiation at 28.7-31.4 kGy.

A 44 year old patient presented with a history of insulin dependent diabetes and a non-healing corneal persistent epithelial defect (PED). A vitrectomy had been performed on the patient which resulted in a scraped cornea. Over the course of approximately three (3) months, the patient was treated with aggressive lubrication therapies with no desired outcomes. Autologous serum drops were prescribed but resulted in no improvement. A bandage contact lens was placed over the defect and resulting in healing; however, once the bandage contact lens was removed, the defect recurred.

An ocular covering was applied to the defect without the use of glue or suture. A bandage contact lens was placed over the ocular covering. At one week post-application, the ocular covering was fully incorporated into the host ocular tissue, and the corneal epithelial defect was completely healed. The patient reported complete relief from pain immediately after application. At eight weeks post-application, the defect was completely healed with no signs of recurrence.

Example 5

Three representative samples of final product for each of three production lots manufactured according to the methods of FIG. 1 were tested for residual ethanol by gas chromatography, analytical method EPA 8260B, CAS No. 64-17-5. Samples were sent to a GLP qualified microbiology laboratory registered with the FDA and third-party accredited to ISO 17025 standards.

The three samples submitted for testing from production lot #1 (2 cm×3 cm; 2 cm×3 cm; and 1.5 cm×2 cm) included amniotic membranes that had been immersed in an alcohol composition comprising 95.5% ethanol for a period of 110 hours. The three samples submitted for testing from production lot #2 (2 cm×3 cm each) included amniotic membranes that had been immersed in an alcohol composition comprising 95.5% ethanol for a period of 25.5 hours. The three samples submitted for testing from production lot #3 (2 cm×3 cm each) included amniotic membranes that had been immersed in an alcohol composition comprising 95.5% ethanol for a period of 24.9 hours.

Zero headspace extraction was performed with double deionized water as the vehicle extractant. Extraction vessels were tumbled during the entire extraction process. For each of the three production lots, the samples were pooled, and one test article was extracted with a weight of 0.05 g and fluid amount of 50 ml. The starting extraction temperature was 22° C. and the ending extraction temperature was 23° C. The extractions lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

The certificates of analyses for production lots #1, #2 and #3 indicated no detectable amounts of ethanol at the minimum reporting limit (0.5 mg/L). The results are summarized in Table 3 below.

TABLE 3

Ethanol Determination for Production Lots #1, #2 and #3

| Production Lot | Total Time in Ethanol | Weight of Sample | Volume of Fluid | Starting Extraction Temperature | Ending Extraction Temperature | Duration of Extraction | Sample Results |
|---|---|---|---|---|---|---|---|
| 1 | 110.0 Hours | 0.05 g | 50 mL | 22° C. | 23° C. | 24 Hours | ND* |
| 2 | 25.5 Hours | 0.05 g | 50 mL | 22° C. | 23° C. | 24 Hours | ND* |
| 3 | 24.9 Hours | 0.05 g | 50 mL | 22° C. | 23° C. | 24 Hours | ND* |

*ND = Not Detected at the Minimum Reporting Limit (0.5 mg/L)

Example 6

Three representative samples of final product manufactured according to the methods of FIG. 1 were tested for residual ethanol by gas chromatography. Samples were sent to a GLP qualified microbiology laboratory registered with the FDA and third-party accredited to ISO 17025 standards.

The three samples submitted for testing were each 2 cm×3 cm and included amniotic membranes that had been immersed in an alcohol composition comprising 100% ethanol for a period of 167.3 hours. The first sample weighed 0.0027 g with an extraction volume of 1.3950 g (assuming that 1 gram=1 milliliter at 20° C.). The second sample weighed 0.0018 with an extraction volume of 1.3705 g (assuming that 1 gram=1 milliliter at 20° C.). The third sample weighed 0.0045 g with an extraction volume of 1.3598 g (assuming that 1 gram=1 milliliter at 20° C.). The ethanol limit of detection (LOD) was 0.2 ppm. Each of the three samples exhibited total ppm of <0.2 ppm. Thus, no ethanol was detected at the minimum reporting limit for any of the three samples.

I claim:
1. A method of treating an ocular wound comprising the step of:
   placing an ocular covering comprising at least one intact, chemically dehydrated amnion membrane on or around a wound site located on or around a portion of an eye or tissue surrounding an eye,
   wherein the ocular covering lacks cross-linking to allow the ocular covering to be resorbed at the wound site within seven days after placement, and
   wherein the ocular wound is a defect resulting from pterygium removal, anterior basement membrane dystrophy, recurrent corneal erosions, non-healing corneal persistent epithelial defect, corneal dystrophy, severe keratitis sicca, or chronic dry eye.

2. The method of claim 1, wherein the amnion membrane is chemically dehydrated in at least one alcohol composition comprising from about 90% to about 100% ethanol.

3. The method of claim 1, further comprising the step of placing a bandage contact lens over the ocular covering.

* * * * *